(12) United States Patent
Patel et al.

(10) Patent No.: US 10,786,289 B2
(45) Date of Patent: Sep. 29, 2020

(54) SYSTEM AND METHODS FOR POSITIONING OF TWO OR MORE INTERACTING ELEMENTS

(71) Applicant: The Regents of the University of Colorado, a Body Corporate, Denver, CO (US)

(72) Inventors: Vikas Patel, Denver, CO (US); Jay Nanninga, Monrovia, MD (US)

(73) Assignee: The Regents of the University of Colorado a Body Corporate, Denver, CO (US)

(*) Notice: Subject to any disclaimer, the term of this patent is extended or adjusted under 35 U.S.C. 154(b) by 565 days.

(21) Appl. No.: 15/325,822

(22) PCT Filed: Jul. 16, 2015

(86) PCT No.: PCT/US2015/040729
§ 371 (c)(1),
(2) Date: Jan. 12, 2017

(87) PCT Pub. No.: WO2016/011241
PCT Pub. Date: Jan. 21, 2016

(65) Prior Publication Data
US 2017/0164988 A1  Jun. 15, 2017

Related U.S. Application Data

(60) Provisional application No. 62/025,163, filed on Jul. 16, 2014.

(51) Int. Cl.
*A61B 17/80* (2006.01)

(52) U.S. Cl.
CPC ................. *A61B 17/8057* (2013.01)

(58) Field of Classification Search
CPC ........... A61B 17/8057; A61B 17/8052; A61B 17/8033; A61B 17/8019
USPC .................................................. 606/289–295
See application file for complete search history.

(56) References Cited

U.S. PATENT DOCUMENTS

| | | | | |
|---|---|---|---|---|
| 10,561,450 B2* | 2/2020 | Thiel | ........... | A61B 17/8009 |
| 2005/0131410 A1* | 6/2005 | Lin | ........... | A61B 17/7032 |
| | | | | 606/266 |
| 2006/0116678 A1* | 6/2006 | Impellizzeri | ........ | A61B 17/8057 |
| | | | | 606/291 |
| 2007/0073297 A1* | 3/2007 | Reynolds | ........... | A61B 17/8052 |
| | | | | 606/280 |
| 2007/0239163 A1* | 10/2007 | Strnad | ........... | A61B 17/8047 |
| | | | | 606/286 |
| 2008/0015592 A1* | 1/2008 | Long | ........... | A61B 17/8014 |
| | | | | 606/279 |
| 2010/0082070 A1* | 4/2010 | Diez | ........... | A61B 17/80 |
| | | | | 606/286 |
| 2010/0160973 A1* | 6/2010 | Leung | ........... | A61B 17/8014 |
| | | | | 606/289 |
| 2010/0312285 A1* | 12/2010 | White | ........... | A61B 17/8057 |
| | | | | 606/289 |

(Continued)

*Primary Examiner* — Matthew J Lawson
(74) *Attorney, Agent, or Firm* — Nicholas Pfeifer; Smith & Hopen, P.A.

(57) ABSTRACT

A plate including elements for receiving threads of a fastener element such that the fastener element may be positioned close, if not flush, to a surface of the plate allowing placement of the assembly much closer to a joint than previous known methods and without interfering with the function of a joint.

20 Claims, 18 Drawing Sheets

(56) References Cited

U.S. PATENT DOCUMENTS

| | | | |
|---|---|---|---|
| 2011/0015682 A1* | 1/2011 | Lewis | A61B 17/8047 606/305 |
| 2013/0172944 A1* | 7/2013 | Fritzinger | A61B 17/8057 606/286 |
| 2014/0052255 A1* | 2/2014 | DeFalco | A61F 2/447 623/17.16 |
| 2014/0277180 A1* | 9/2014 | Paolino | A61B 17/8057 606/291 |
| 2017/0348023 A1* | 12/2017 | Thiel | A61B 17/683 |

* cited by examiner

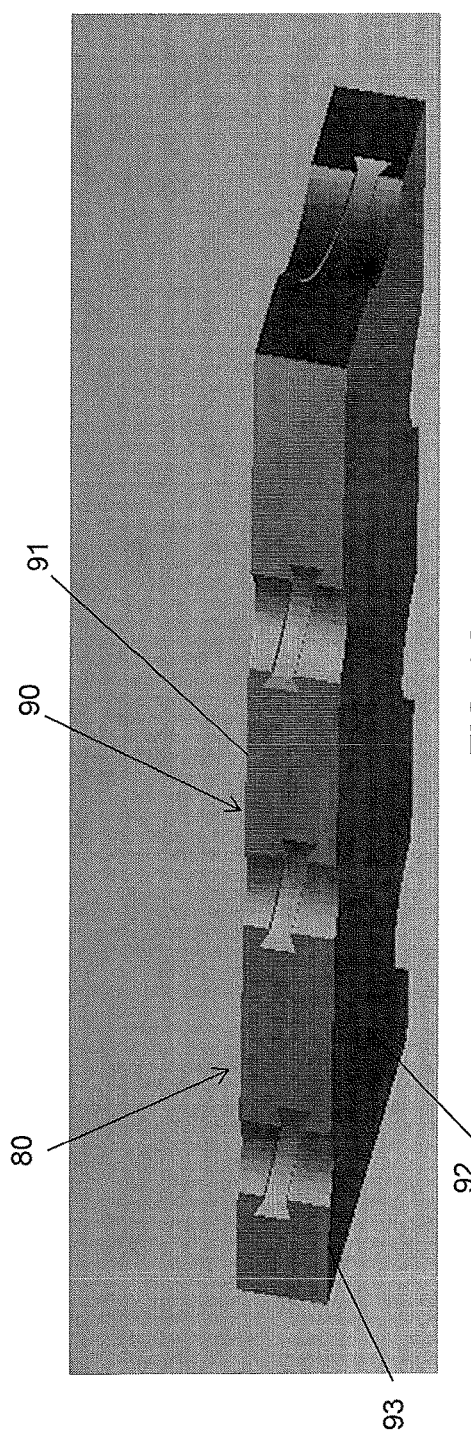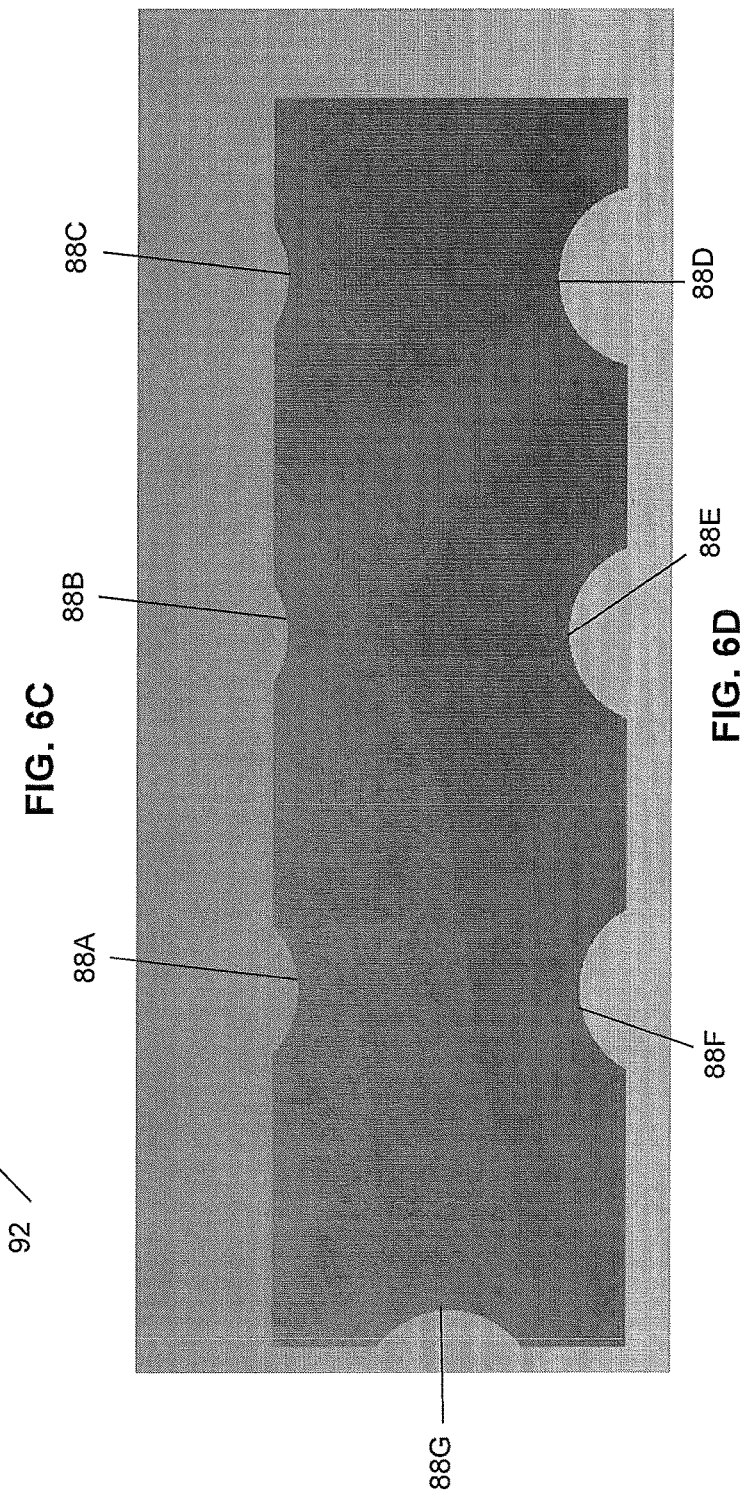
FIG. 6C
FIG. 6D

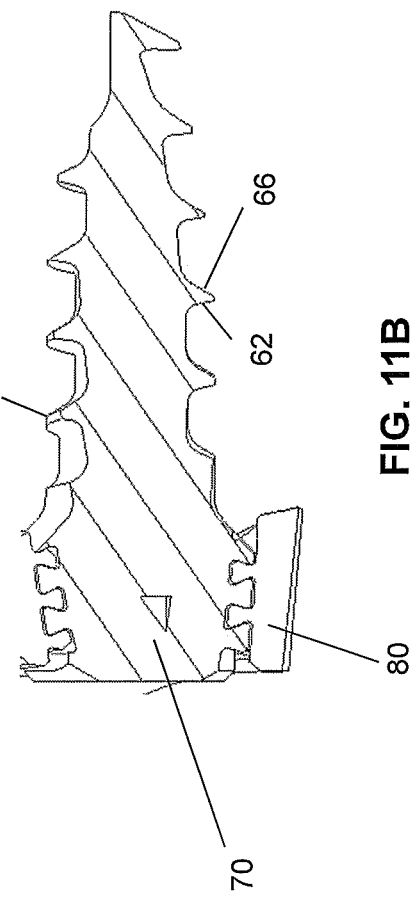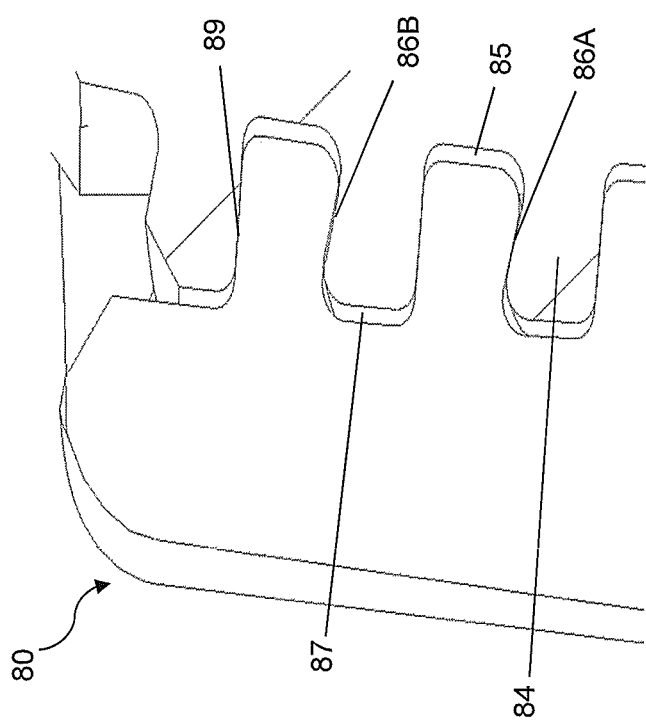
FIG. 11B
FIG. 11A

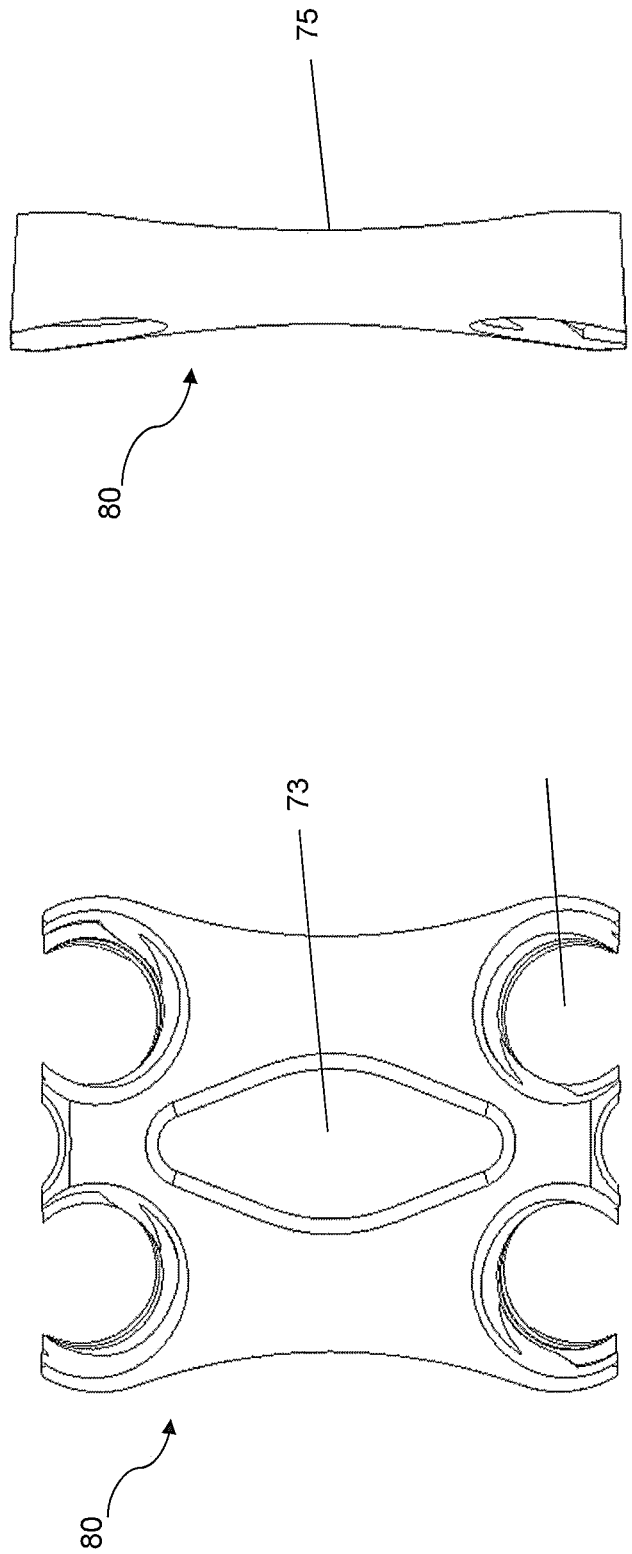
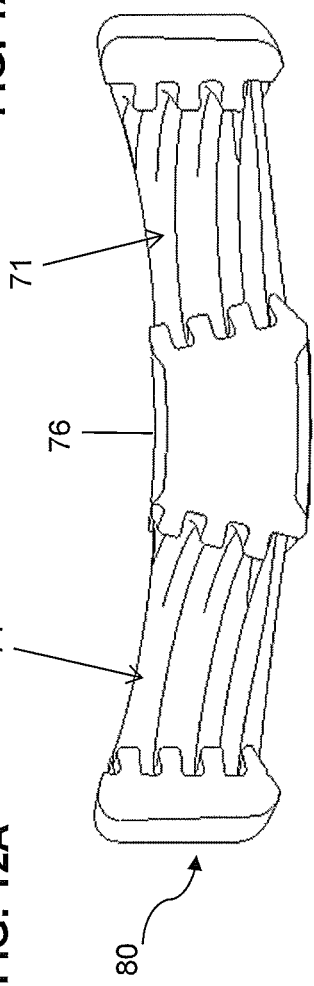
FIG. 12A
FIG. 12B
FIG. 12C

SYSTEM AND METHODS FOR POSITIONING OF TWO OR MORE INTERACTING ELEMENTS

CROSS REFERENCE TO RELATED APPLICATIONS

This application claims the benefit of U.S. Provisional Patent Application 62/025,163 filed Jul. 16, 2014, which is incorporated by reference.

FIELD OF THE INVENTION

The present invention relates generally to system and methods for positioning two or more interacting elements. More specifically, the present invention pertains to implantable orthopedic devices, and more particularly to a plate and fastener element assembly.

BACKGROUND OF THE INVENTION

From time to time, a consumer may be motivated to position two or more elements such that they are configured to maintain a particular position for a considerable period of time, such as a few minutes, a few hours, a few days, or a few weeks. As an example, if a person or animal breaks or fractures a bone, the treatment may include positioning one or more interacting elements relative to the bone to stabilize the bone in an optimized position for healing.

One or more interacting elements may include, for example, a plate and one or more fastener elements for attachment to vertebrae in order to immobilize, stabilize and/or align those vertebrae. The plate may be used for a variety of conditions including for example providing added strength and rigidity after fusion of adjacent vertebrae, securing vertebrae together where an intervening vertebrae has been removed and replaced, correcting spinal deformities, and correcting instability caused by trauma, fractures, tumors, advanced degenerative discs, infection or congenital or acquired deformities.

Plates used for these types of conditions generally span the distance between two, three, four or more vertebrae, as required in a given situation. The plate generally curves so as to fit the curvature of the vertebrae to which they are attached. Additionally, a plate of this type generally matches the curvature of the cervical spine. A plate of this type is typically provided with holes for fastener elements known as "bone screws". Holes are drilled into the adjacent vertebrae by instruments which are known in the art, after which the plate is attached by the bone screws which pass through the holes in the plate for securing the plate to the adjacent vertebrae.

While certain systems for stabilizing a bone exist, such known systems are associated with certain disadvantages. Thus, there is a demand for an improved system and methods for positioning two or more interacting elements relative to one another such as a plate and one or more fastener elements, for use in applications such as stabilizing fractures and cervical fixation to name a few. The present invention satisfies this demand.

SUMMARY OF THE INVENTION

For purposes of this application, the present invention is discussed in reference to one or more interacting elements configured to stabilize the position of a bone in the form of a plate and one or more fastener elements, but the discussion is merely exemplary. The present invention is applicable to any system in which two or more interacting elements are configured to maintain a particular configuration and/or position.

Certain embodiments of the system and method of the present invention include a fastener element with a body component and a thread component. Other embodiments of a fastener element may include multiple body components, each of which may include a respective thread component.

Certain embodiments of a thread component may be configured to maximize the amount of weight the connection between the two interacting components can bear. Other embodiments may be configured to maximize flexibility of the connection between the two interacting components.

One object of certain embodiments of the present invention is that it permits inserting a first interacting element such as a fastener element into a second interacting element such as a plate so that the top surface of the first interacting element is flush with or remains below the top surface of a second interacting element.

Another object of certain embodiments of the present invention is that it facilitates a removable connection between a first interacting element and a second interacting element wherein the first interacting element is connected along the periphery of the second interacting element; for example a fastener element connected along the periphery of the plate.

Advantageously, in embodiments in which the second interacting element is a plate for setting bones, such embodiments permit positioning the plate close to a joint without impinging the adjacent bone in the joint. Another advantage of such embodiments is that it may use smaller plates for setting bones relative to other connection methods, while maintaining strength of the connection. Alternatively, the connection may be a stronger and more rigid interface between the first interacting element and second interacting element relative to other connection methods.

Another object of certain embodiments of the present invention is to include different thread components on the body component of the fastener element defining a first body component and a second body component. The first body component comprises a first thread component that wraps around a first portion of the body component of the fastener element and a second body component comprises a second thread component wrapped around a second portion of the body component.

It is contemplated that a thread component according to the invention may be of a generally helical shape with the same or varying pitch along the length of the body component. For purposes of this application, the pitch of a helix is the width of one complete helix turn, measured parallel to the axis of the helix.

The present invention and its attributes and advantages will be further understood and appreciated with reference to the detailed description below of presently contemplated embodiments, taken in conjunction with the accompanying drawings.

BRIEF DESCRIPTION OF THE DRAWINGS

The preferred embodiments of the invention will be described in conjunction with the appended drawings provided to illustrate and not to the limit the invention, where like designations denote like elements, and in which:

FIG. 6C illustrates a perspective view of an embodiment of an interacting element configured as a plate including a plurality of thread receiving elements;

FIG. 6D illustrates a top view of an embodiment of an interacting element configured as a plate including a plurality of thread receiving elements;

FIG. 11A illustrates an exploded view of a plate including a thread receiving element;

FIG. 11B illustrates a cross-section view of an embodiment of a fastener element engaged with the thread receiving element of a plate;

FIG. 12A illustrates a top view of a plate element;

FIG. 12B illustrates a side view of a plate element;

FIG. 12C illustrates a cross-section view of a plate element;

DETAILED DESCRIPTION OF EMBODIMENTS OF THE INVENTION

For convenience of description, terms such as "above", "below", "upper", "lower", "outer", "inner", "bottom" and "top" are used in this application to refer to the system and the components of the system in an orientation illustrated in the accompanying drawings. However, it will be understood that the embodiments of the invention described in this application advantageously can be used in a variety of orientations.

Certain embodiments of the system 10 and method of the present invention include a first interacting element 40A and a second interacting element 40B.

Figure 1:
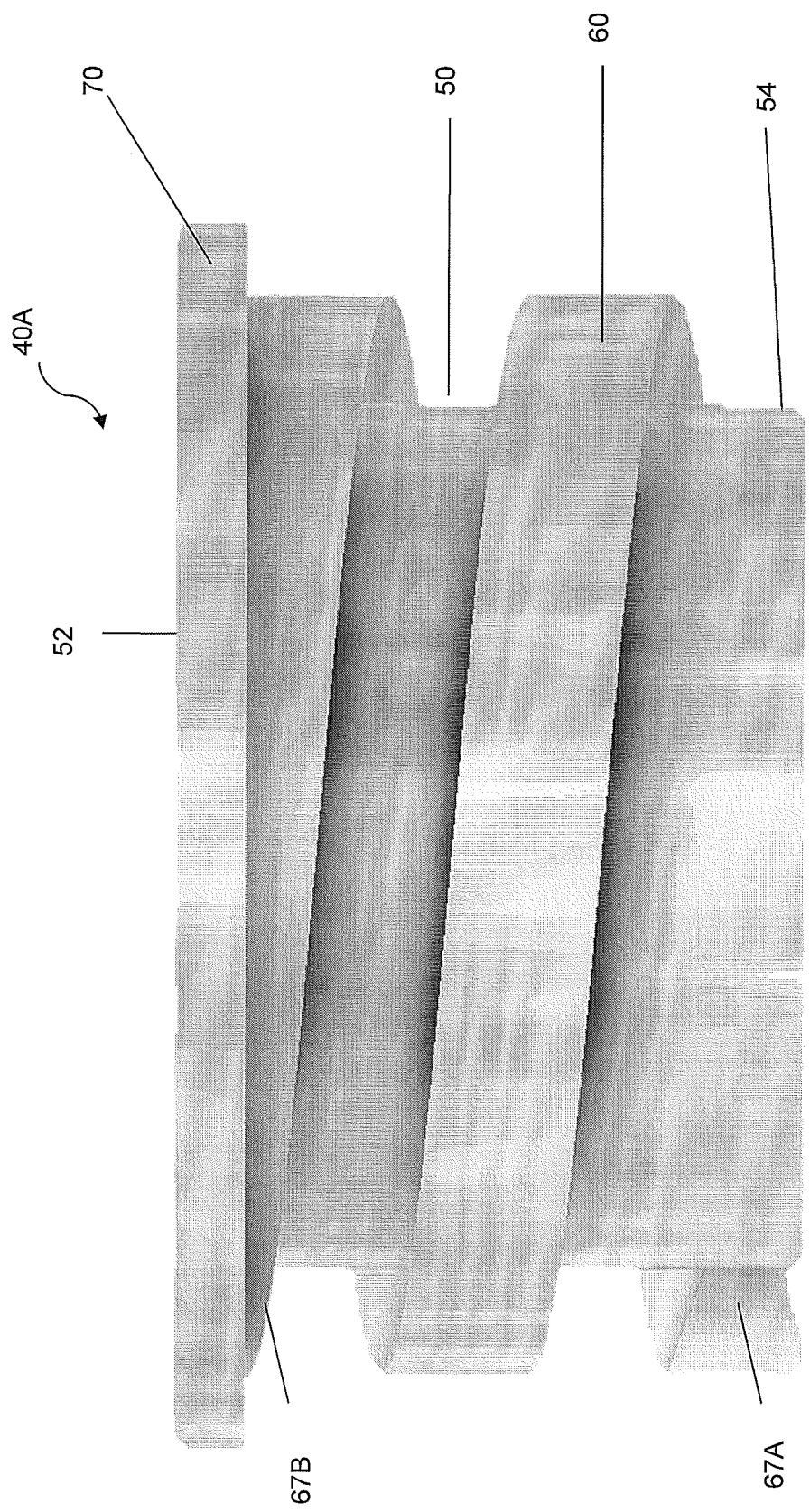
FIG. 1 illustrates an embodiment of a fastener element including a body component and a thread component.

As illustrated in FIG. 1, certain embodiments of a first interacting element 40A may be in the form of a fastener element 70 and include a body component 50 and a thread component 60.

The body component 50 may include an end cap element 52 and a core body element 54. The core body element 54 may be configured as the foundation on which the thread component 60 is positioned or formed adjacent to the thread component 60.

Figure 5:
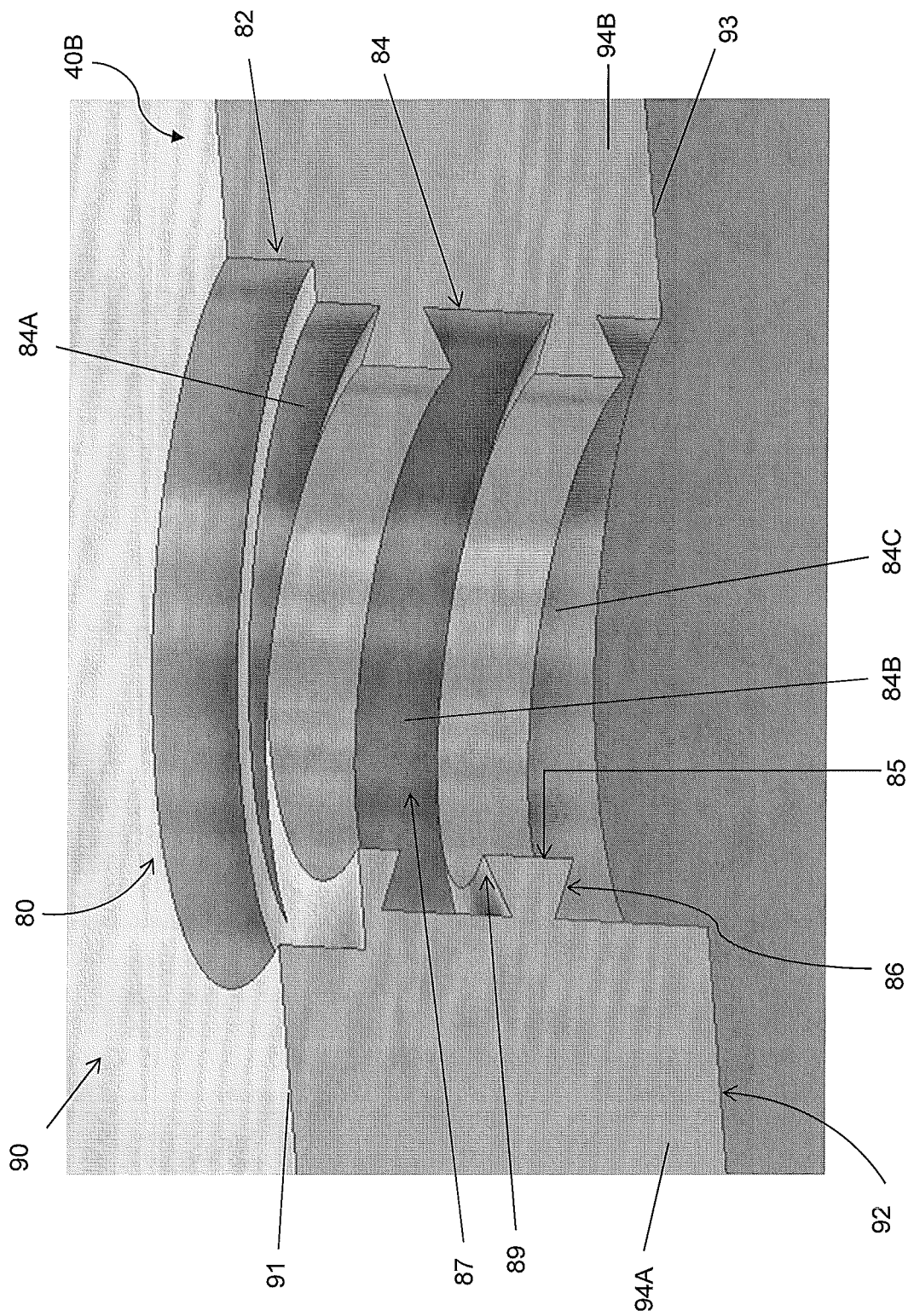
FIG. 5 illustrates an embodiment of a thread receiving element of an interacting element.

The end cap element 52 may be configured to be relatively wider than the core body element 54 such that the end cap element 52 effectively forms the end of the thread component 60 and the first interacting element 40A cannot be rotated any further when the end cap element 52 meets with an end cap receiving element 82 in a second interacting element 40B (see e.g., FIG. 5). Other embodiments may include no end cap element or an end cap element that has the same or smaller cross-section diameter than the core body element 54.

The thread component 60 may include a thread termination end 67A and a thread origination end 67B. The thread component 60 is positioned relative to the body component 50 such that upon rotating the first interacting element 40A, the thread component 50 is received by a thread receiving element 84 in the second interacting element 40B (see e.g., FIG. 5).

Figure 2:
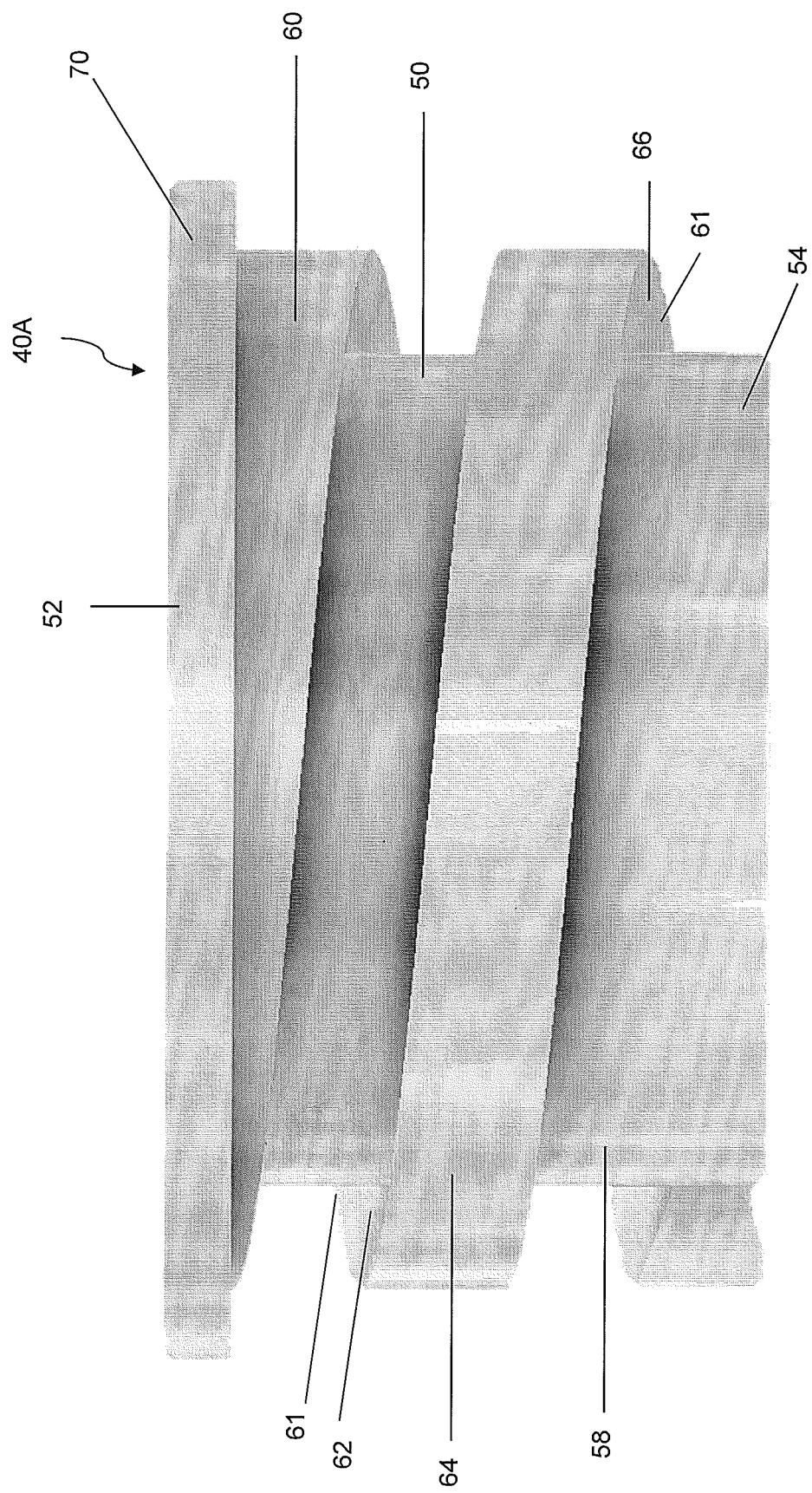
FIG. 2 illustrates additional features of a fastener element including a body component and a thread component.

As illustrated in FIG. 2, the thread component 60 may include an outer thread surface 64 that may be generally parallel to the outer core body surface 58 of the core body element 54. In addition, the thread component 60 may include two or more side thread surfaces 61 configured to adjoin the outer thread surface 64 to the outer core body surface 58. The embodiment illustrated in FIG. 2 includes an upper thread surface 62 and a lower thread surface 66.

In certain embodiments, the entire first interacting element is a single unit formed by, for example, injection molding. In other embodiments, certain portions of the first interacting element are formed separately from the thread component and then the pieces are attached together.

Figure 3A:
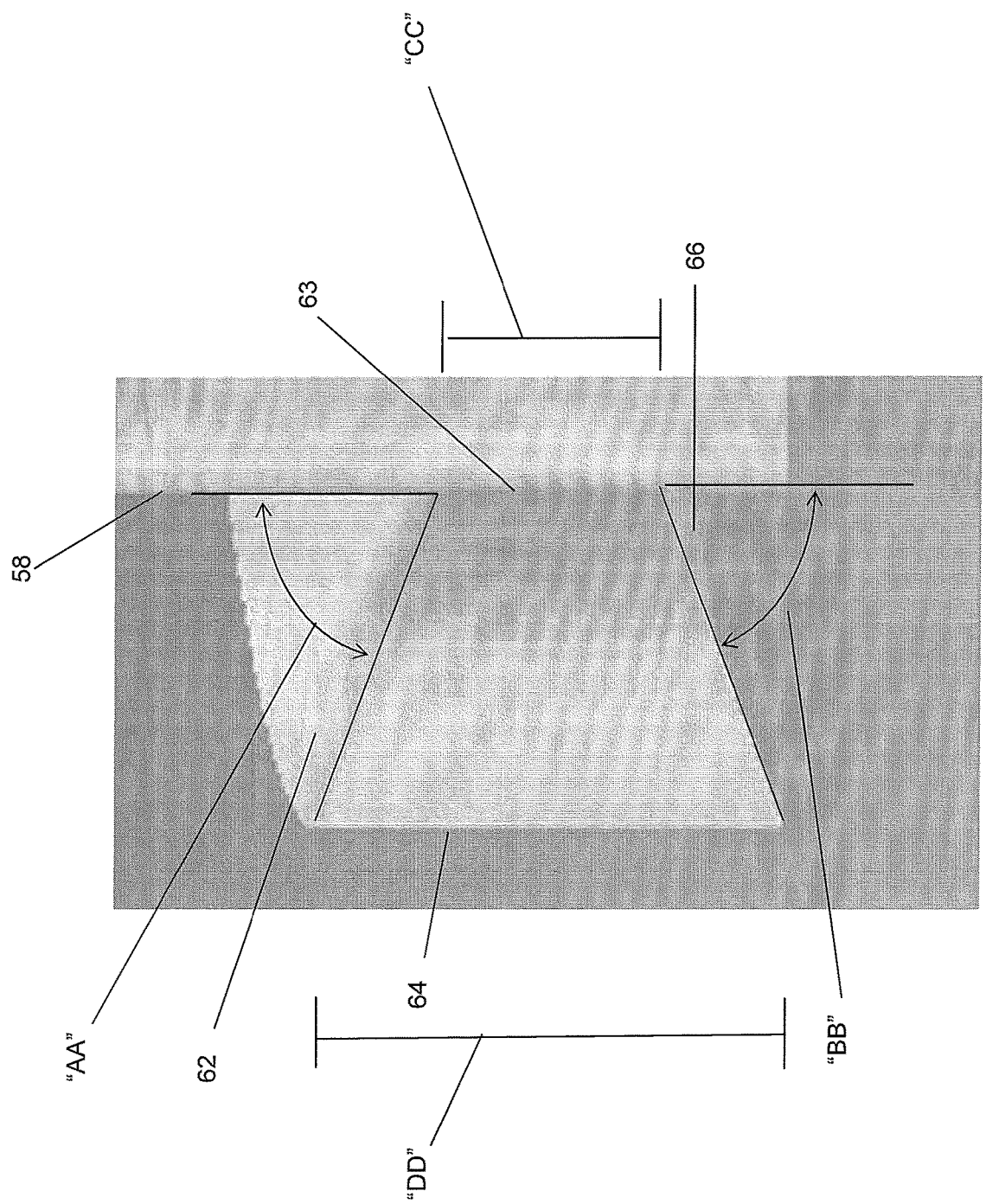
FIG. 3A illustrates a magnified view of a thread component.

As illustrated in FIG. 3A, a thread component 60 also may include a thread base surface 63. In certain embodiments, the thread base surface 63 is generally continuous with the outer core body surface 58. In other embodiments, the thread base surface 63 is a surface from the outer core body surface 58, but may be attached to the outer core body surface 58.

The angle between the upper thread surface 62 and the outer core body surface 58 is an upper thread angle "AA". The angle between the lower side thread surface 66 and the outer core body surface 58 is a lower thread angle "BB". In certain embodiments, the upper thread angle "AA" is between 45 and 90 degrees and the lower thread angle "BB" is between 45 and 90 degrees. In certain embodiments, the upper thread angle "AA" or the lower thread angle "BB" is 60 degrees.

As also illustrated in FIG. 3A, the length "CC" of the thread base surface 63 may be 0.102 millimeters (mm), 0.300 mm, or 0.700 mm. In certain embodiments, the length "DD" of the outer thread surface 64 is 0.318 mm, 0.875 mm, or 1.275 mm at its widest point. Of course, the length "DD" of the outer thread surface 64 may be shorter or longer, e.g., near the upper or lower sections of the core body element 54. As some examples, the ratio of the length "CC" of the thread base surface 63 to the length "DD" of the outer thread surface 64 may be 0.102 mm:0.318 mm, 0.300 mm:0.875 mm, or 0.700 mm:1.275 mm.

In certain embodiments, the size of the thread component 60 is static throughout the entire thread component 60. In other embodiments, the thread base surface 63 (and possibly the outer thread surface 64) is smaller in length near the termination end 67A and larger in length near the origination end 67B (see FIG. 1). The length of each thread component surface may increase continuously (e.g. taper continuously) throughout the length of the thread component 60 or may increase more sharply only near the origination end 67B. Such embodiments are configured to permit locking the thread component 60 into a thread receiving element 84 (shown in FIG. 5) when the larger portion of the thread component meets with or is compressed into the thread receiving element 84.

Figure 3B:
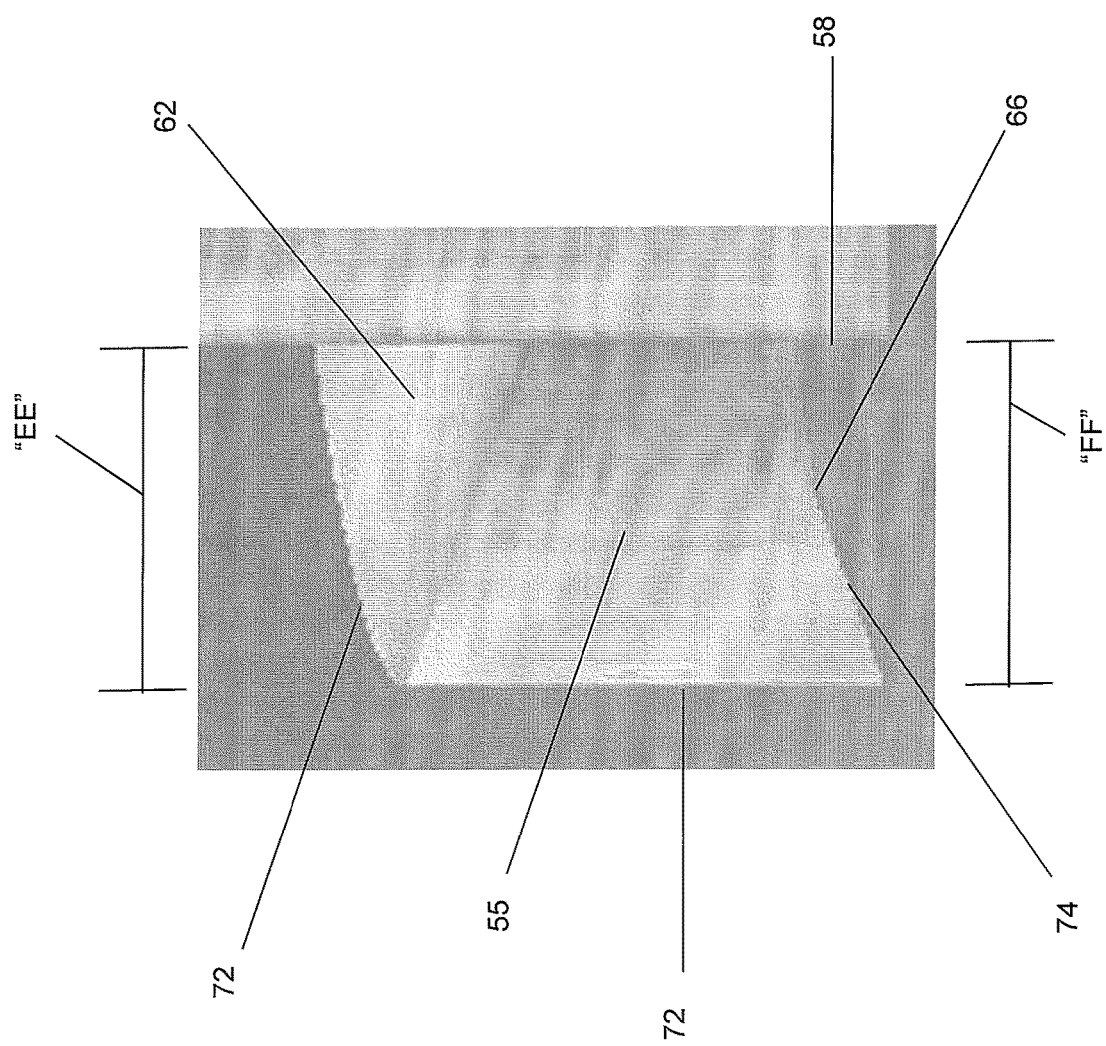
FIG. 3B also illustrates a magnified view of a thread component.

As illustrated in FIG. 3B, certain embodiments of the upper thread depth "EE" between the upper thread edge 72—that is, the edge at which the upper thread surface 62 meets the outer core body surface 58—may be 0.188 millimeters or 0.498 millimeters. Also, the lower thread depth "FF" between the lower thread edge 74—that is, the edge at which the lower side thread surface 66 meets the outer core body surface 58—may be 0.188 millimeters or 0.498 millimeters. The upper thread depth "EE" may be equal to, greater than, or less than the lower thread depth "FF".

The upper thread surface 62, lower thread surface 66, and outer thread surface 64 together form a thread profile 55 (from the side view). In certain embodiments, the thread profile 55 of the thread component 60 may be shaped in a dovetail shape. In certain embodiments of the present invention, any surface, including the upper thread surface 62, lower thread surface 66, outer thread surface 64, may be linear or curved.

Figure 4:
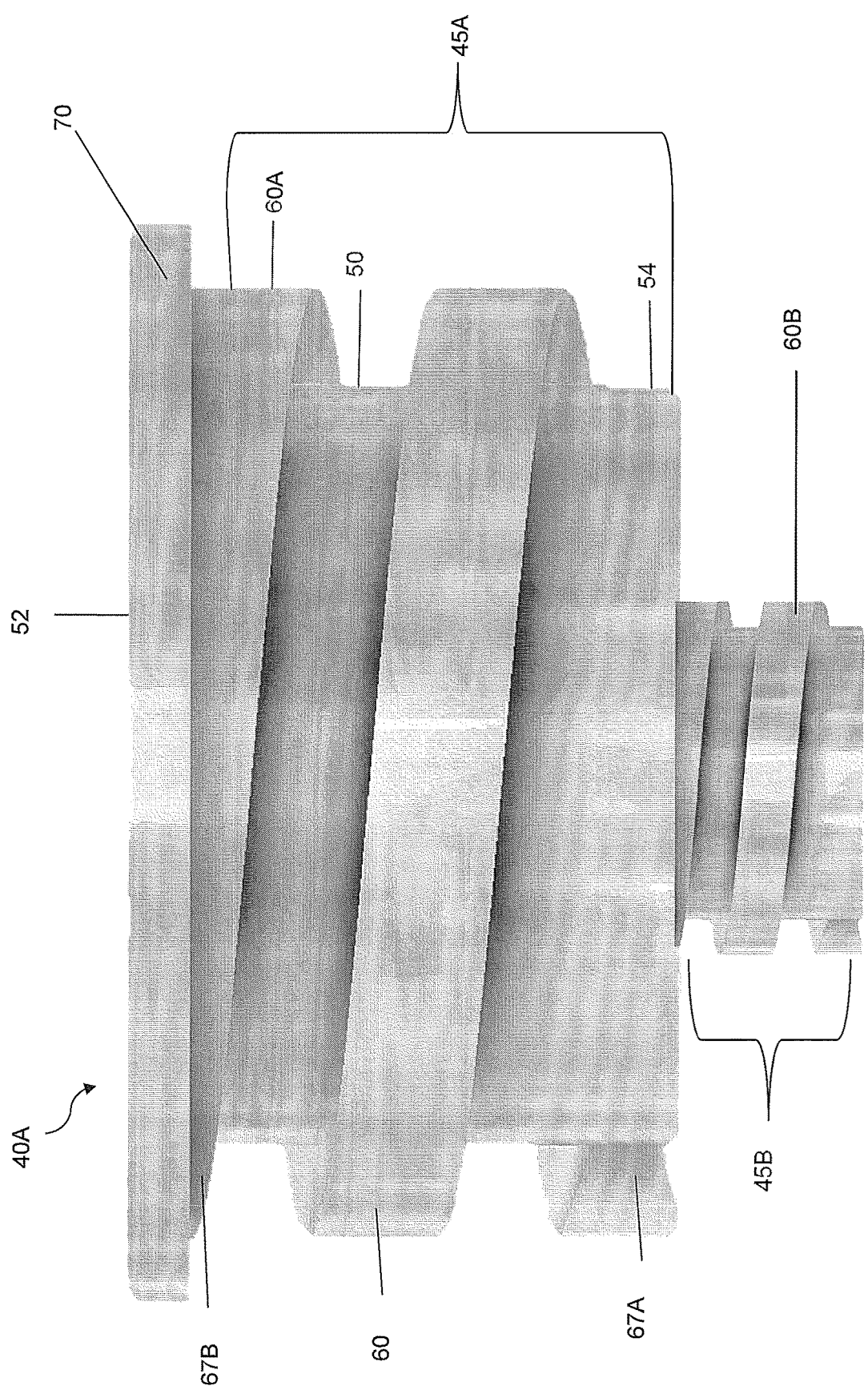
FIG. 4 illustrates an embodiment of a fastener element having a first body component and a second body component.
Figure 8A:
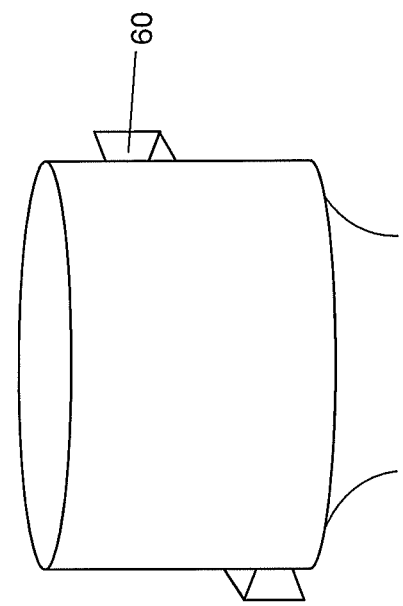
FIG. 8A illustrates another embodiment of an interacting element having a first body component and a second body component, wherein the thread component on the first body component includes only a partial turn of a helix.
Figure 8B:
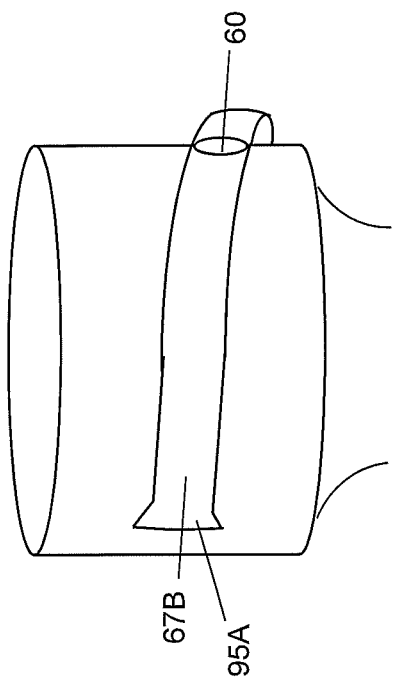
FIG. 8B illustrates an additional embodiment of an interacting element having a first body component and a second body component, wherein the thread component on the first body component includes only a partial turn of a helix.
Figure 8C:
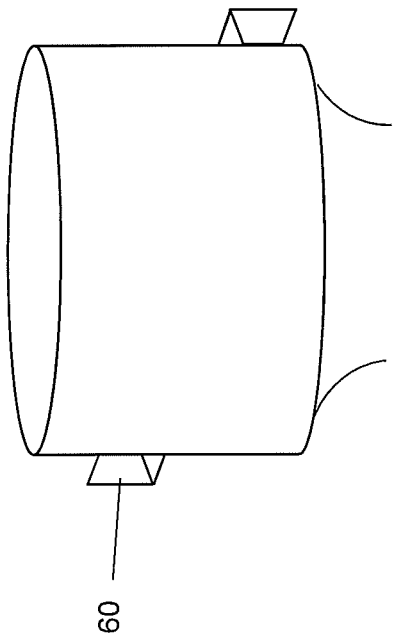
FIG. 8C illustrates another embodiment of an interacting element having a first body component and a second body component, wherein the thread component on the first body component includes only a partial turn of a helix.

Certain embodiments of the present invention include two body components such as that shown in FIG. 4 (see also FIG. 8A, FIG. 8B). Turning to FIG. 4, a second body component 45B including a second thread component 60B configured to have a smaller cross-section diameter than the cross-section diameter of the first body component 45A including a first thread component 60A. Such embodiments may be configured such that the first body component 45A is configured to interact with a first thread receiving element such as a plate and the second body component 45B is configured to interact with a second thread receiving element such as a bone). For example, a plate 80 (see FIG. 14A) may be positioned relative to a bone to promote healing of the bone. The system of the present invention may be configured to stabilize the position of the plate relative to the bone. In such embodiments, the second thread component 60B of the second body component 45B may be any size or shape, including dovetail, rounded, v-shaped, pedicle, or other. In certain embodiments, the second thread component 60B has the same pitch as the pitch of the first thread component 60A of the first body component 45A. In other embodiments, the second thread component 60B has a greater pitch than the first thread component 60A such that the plate may be compressed against the bone as the core body component is interacting with the plate. An example of a pitch measurement of certain embodiments includes a 1.25 mm pitch on the second interacting element (or plate). Such a plate embodiment may have a peripheral surface length of 5 mm. The pitch of the thread component 60B on the second body component 45B may influence the pitch of the thread component 60A on the first body component 45A.

In certain embodiments, a first thread component 60A may be continuous with or connected to the second thread component 60B via a thread-thread connector (not shown). The thread-thread connector may have a tapered shape. In other embodiments, the two thread components 60A, 60B are completely integrated and have no connection.

FIG. 5 illustrates a cross-section of an example of a second interacting element 40B in the form of a plate 80 such as that used for setting a bone. The plate 80 may include an end cap receiving element 82 and a thread receiving element 84. The end cap receiving element 82 may be generally complementary to the size and shape of the end cap element 52. The thread receiving element 84 may be generally complementary to the size and shape of the thread component 60.

Each thread receiving element 84 may include an outer receiving surface 85, upper receiving surface 86, inner receiving surface 87, and lower receiving surface 89. In certain embodiments of the present invention, any surface, including the outer receiving surface 85, upper receiving surface 86, inner receiving surface 87, and lower receiving surface 89 may be linear or curved.

Figure 7:
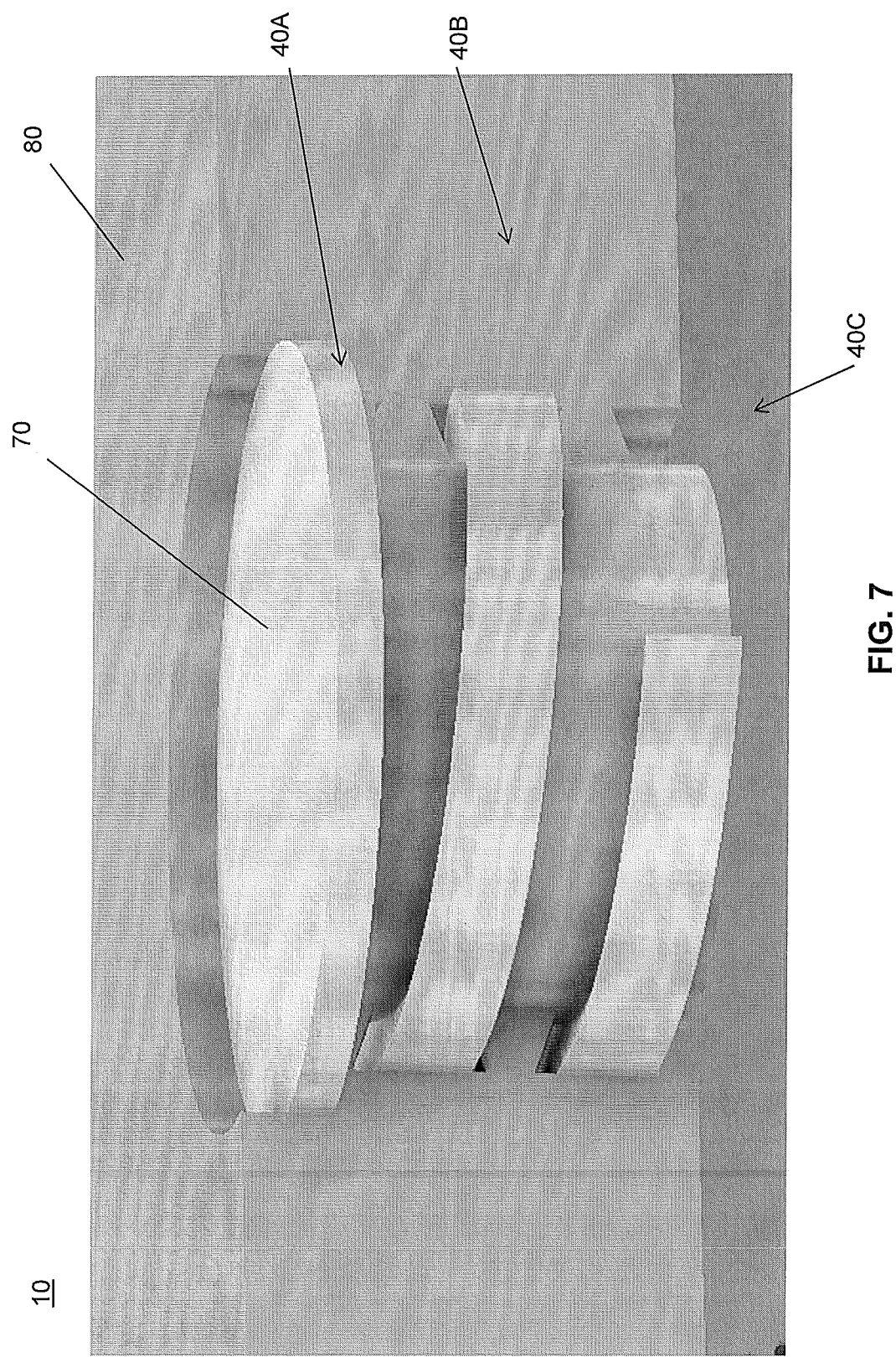
FIG. 7 illustrates an interacting element positioned relative to a first thread receiving element.

When the thread component 60 is received within the thread receiving element 84 (as illustrated in FIG. 7), the outer receiving surface 85 is generally adjacent to or flush with the outer core body surface 58 of the core body element 54, the upper receiving surface 86 is generally adjacent to or flush with the lower thread surface 66, the inner receiving surface 87 is generally adjacent to or flush with the outer thread surface 64, and the lower receiving surface 89 is generally adjacent to or flush with the upper thread surface 62.

In embodiments in which the thread component 60 includes multiple helical turns, the thread receiving element 84 may include more than one thread receiving element 84, such as a first thread receiving element 84A, a second thread receiving element 84B, and a third thread receiving element 84C. Any number of thread receiving elements 84 is contemplated. In the embodiment illustrated in FIG. 5, the first thread receiving element 84A is positioned closest to the upper surface 90 of the plate 80. The third thread receiving element 84C is positioned closest to the lower surface 92 of the plate 80. A second thread receiving element 84B is positioned between the first thread receiving element 84A and the third thread receiving element 84C. The third thread receiving element 84C may be tapered in size such that the respective portion of the thread component 60 may be stabilized in position.

In certain embodiments, the one or more thread receiving elements 84 are positioned along the periphery of plate 80 such that only certain portions of the thread component 60 are enclosed within a thread receiving element 84. One or more thread receiving elements 84 may be flanked by a first peripheral surface 94A and a second peripheral surface 94B of the plate 80.

The peripheral surfaces 94A, 94B meet with the upper surface 90 at an upper edge 91 and a lower surface 92 at a lower edge 93.

Figure 6A:
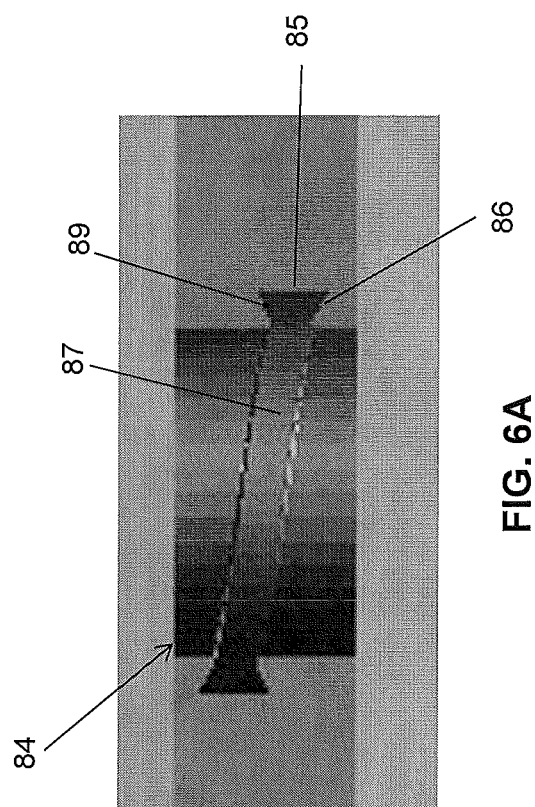
FIG. 6A illustrates a side view of an embodiment of an interacting element configured as a plate including a thread receiving element.
Figure 6B:
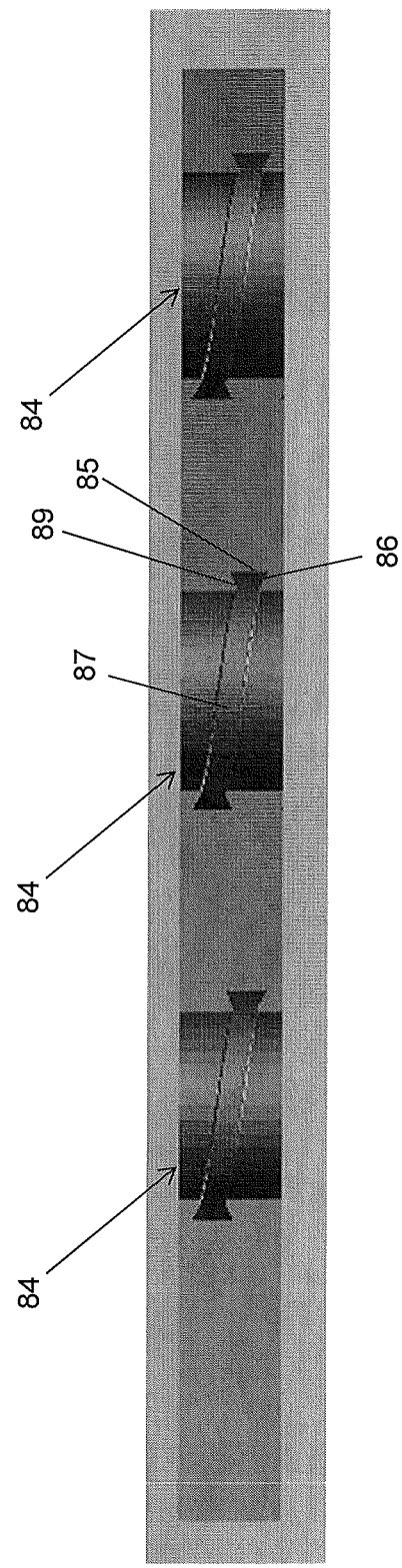
FIG. 6B illustrates a side view of an embodiment of an interacting element configured as a plate including a plurality of thread receiving elements.

Additional embodiments may be configured to include only one thread receiving element 84 such as that illustrated in FIG. 6A. Certain other embodiments of a bone-setting plate 80 according to the invention include more than one thread receiving element 84 as illustrated in FIG. 6B—FIG. 6D. The thread receiving element 84 embodiments shown in FIG. 6A—FIG. 6D may receive a thread component 60 shaped in multiple helical turns, for example, turns that start at or near the bottom side of the first body component and end at or near the top side of the first body component. Alternatively, the thread receiving element 84 embodiments shown in FIG. 6A-FIG. 6D may receive a thread component 60 shaped in a single helical turn or less than a full helical turn. For purposes of this application, a "full helical turn" is a complete 180 degree rotation in around a cylindrical axis. (Obviously, if the rotation was in a flat plane instead of a cylindrical axis, the shape would be a circle, not a helix.)

FIG. 6D shows a few examples of shape configurations of a thread receiving element 84 or, more specifically, the top profile shown by 88 of a thread receiving element 84. Clearly, the top profile 88 may form a general arc-shape configuration. In certain embodiments, the arc-shape configuration may be any portion of a circle from 360 degrees to 90 degrees, including, for example, a three-quarters-circle shape (270 degrees), half-circle-shape (180 degrees), third-circle shape (120 degrees), or fourth-circle shape (90 degrees). While the embodiment in FIG. 6D illustrates multiple thread receiving elements 84, each having a different arc-shape configuration 88A-88G, it is contemplated that plate 80 may include a plurality of thread receiving elements 84 each having the same arc-shape configuration 88.

FIG. 7 illustrates a system 10 including a first interacting element 40A configured as a fastener element 70 positioned within the second interacting element 40B configured as a plate 80 for setting bones. Certain embodiments include a third interacting element 40C, which may be a bone. For example, the fastener element 70 may be configured to interact with both a plate 80 and a bone—shown as third interacting element 40C. In certain embodiments, the fastener element 70 may be configured to interact with only the plate 80. In certain other embodiments the fastener element 70 may be configured to only interact with bone (i.e., without the use of plate 80).

Figure 8D:
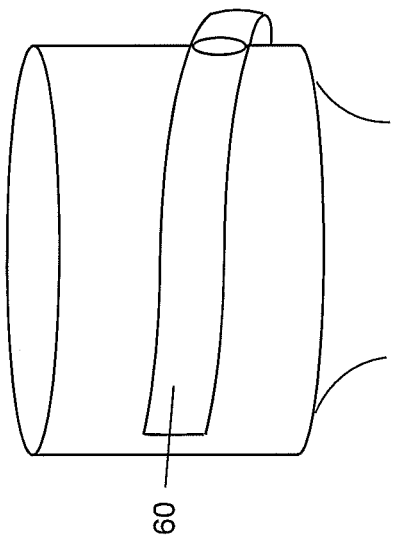
FIG. 8D illustrates an additional embodiment of an interacting element having a first body component and a second body component, wherein the thread component on the first body component includes only a partial turn of a helix and the thread component includes a stop element.

As illustrated in FIG. 8A and FIG. 8B, the helical shape of the thread component 60 may be left-handed or right-handed. Also illustrated in FIG. 8A, FIG. 8B, FIG. 8C and FIG. 8D, the thread component 60 may be sized to include only a partial turn of a helix shape. As also illustrated in FIG. 8D, the thread origination end 67B may include an enlarged portion to form a stop element 95A such that the thread component 60 cannot move further into the thread receiving component 84.

Figure 9A:
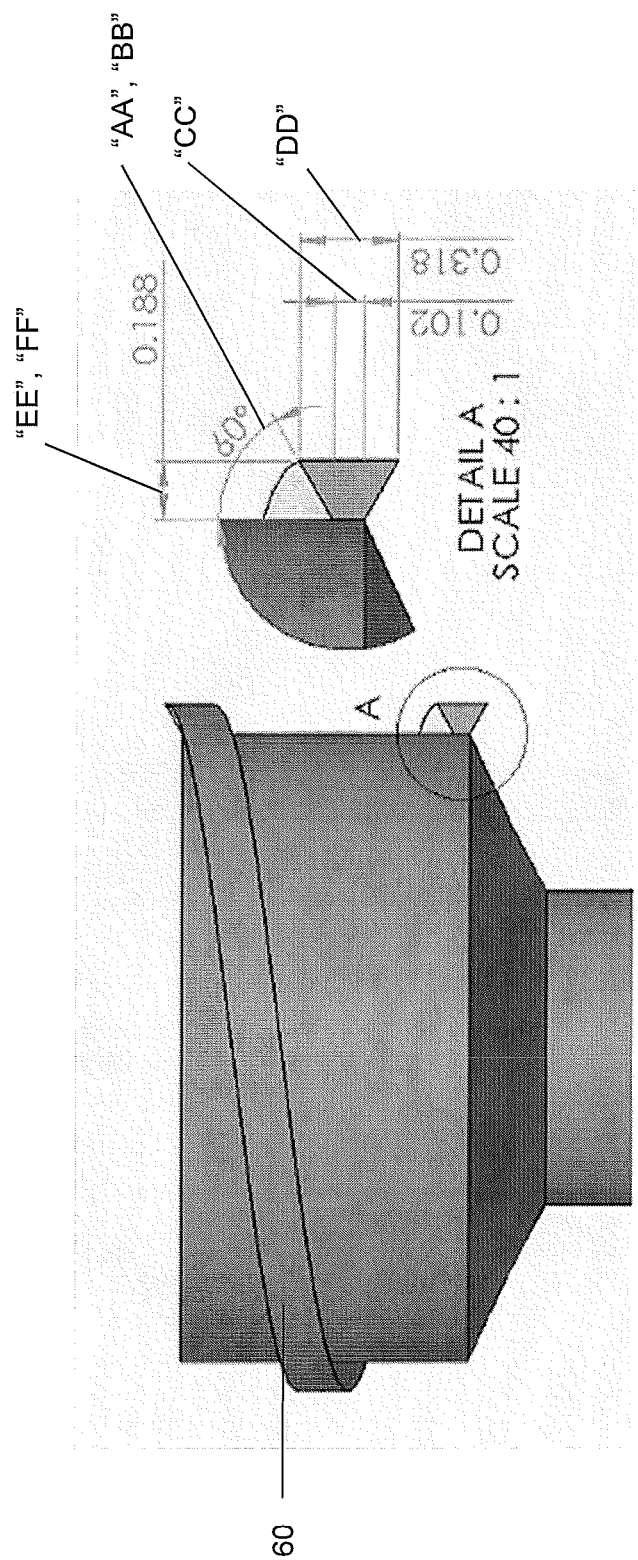
FIG. 9A illustrates an additional embodiment of an interacting element having a first body component and a second body component.
Figure 9B:
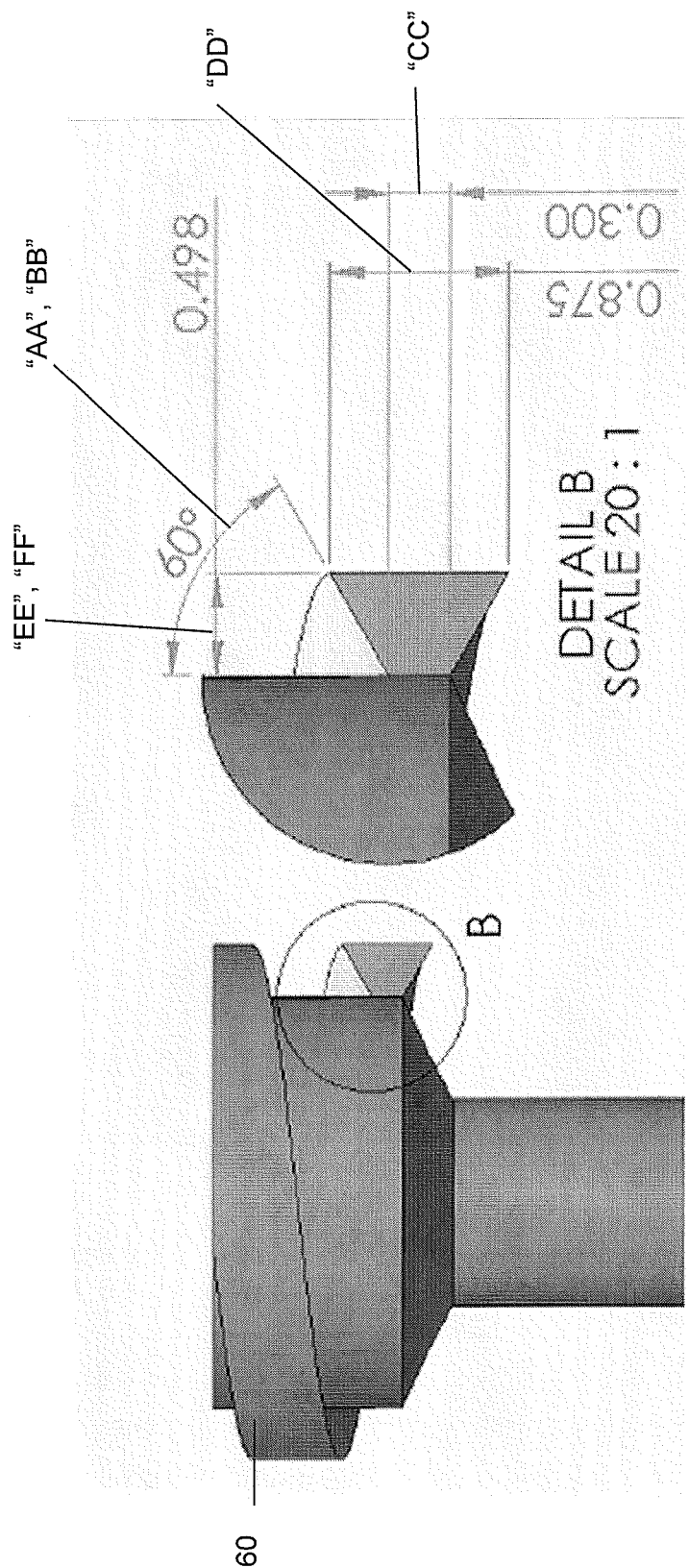
FIG. 9B illustrates another embodiment of an interacting element having a first body component and a second body component.
Figure 9C:
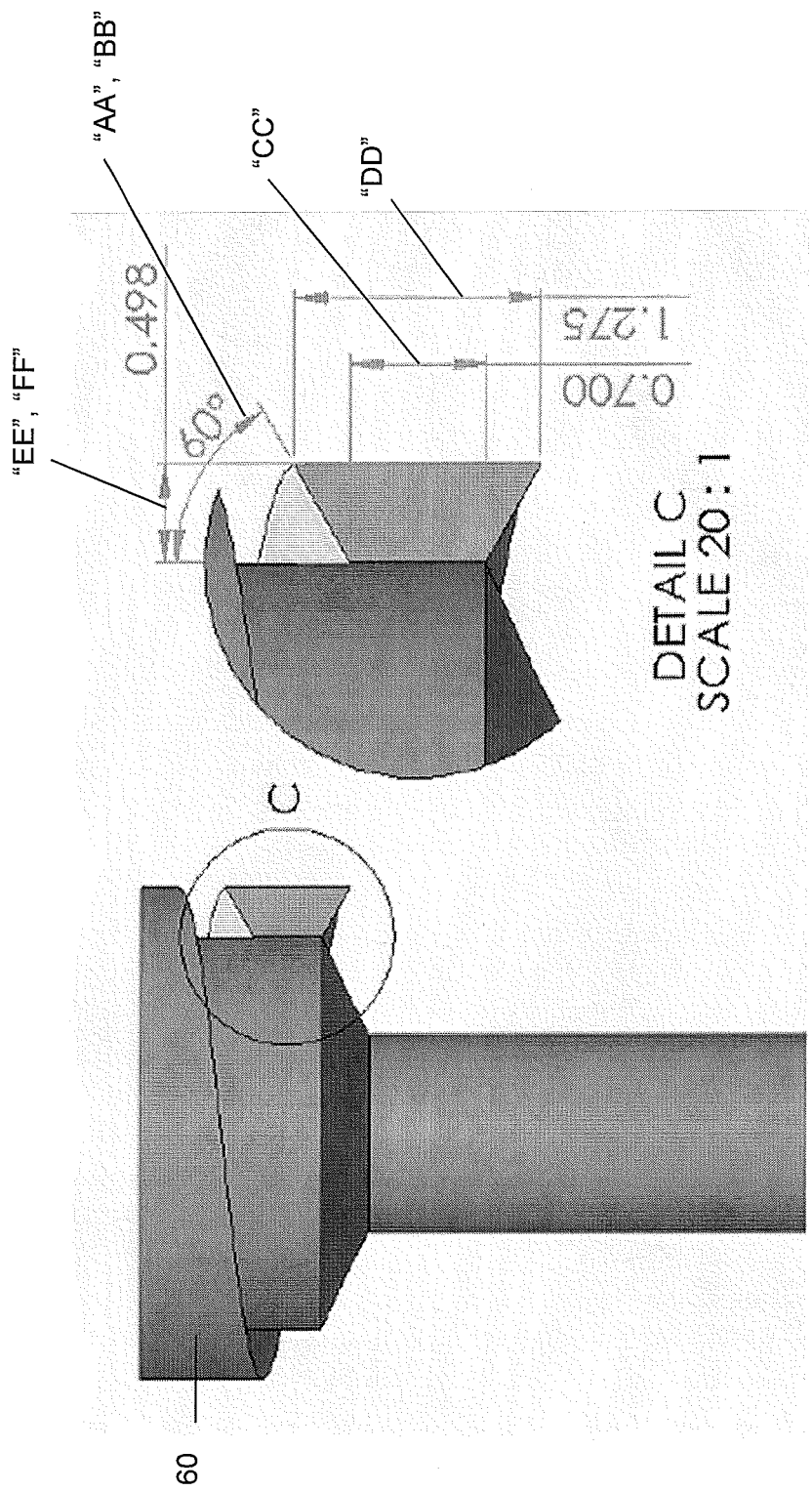
FIG. 9C illustrates an additional embodiment of an interacting element having a first body component and a second body component.

FIG. 9A, FIG. 9B, and FIG. 9C illustrate additional embodiments of the present invention. While certain embodiments are identified as having specific measurements in millimeters (mm), each part of the invention may be sized and shaped for any particular purpose. Specifically, in certain embodiments, the measurements are scaled up or scaled down based on the ratios illustrated in FIGS. 9A-9C, sometimes for a particular purpose (e.g., stronger connection or more flexibility). In addition, the ratios between components may be altered to achieve a particular purpose (e.g., stronger connection or more flexibility) as well.

For example, turning to FIG. 9A, the upper thread angle ("AA") and/or lower thread angle ("BB") may be about 60 degrees. The length of the thread base surface ("CC") may be about 0.102 mm and the length of the outer thread surface ("DD") about 0.318 mm. The upper thread depth ("EE") and/or lower thread depth ("FF") may be about 0.188 mm.

Turning to FIG. 9B, the upper thread angle ("AA") and/or lower thread angle ("BB") may be about 60 degrees. The length of the thread base surface ("CC") may be about 0.300 mm and the length of the outer thread surface ("DD") about 0.875 mm. The upper thread depth ("EE") and/or lower thread depth ("FF") may be about 0.498 mm.

In another example shown in FIG. 9C, the upper thread angle ("AA") and/or lower thread angle ("BB") may be about 60 degrees. The length of the thread base surface ("CC") may be about 0.700 mm and the length of the outer thread surface ("DD") about 1.275 mm. The upper thread depth ("EE") and/or lower thread depth ("FF") may be about 0.498 mm.

Figure 10A:
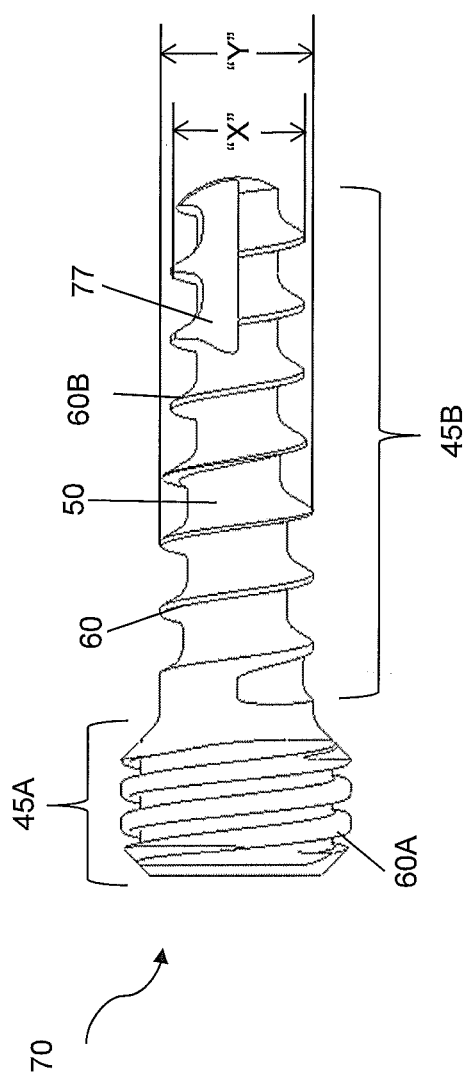
FIG. 10A illustrates an embodiment of an interacting element having a first body component and a second body component.
Figure 10B:
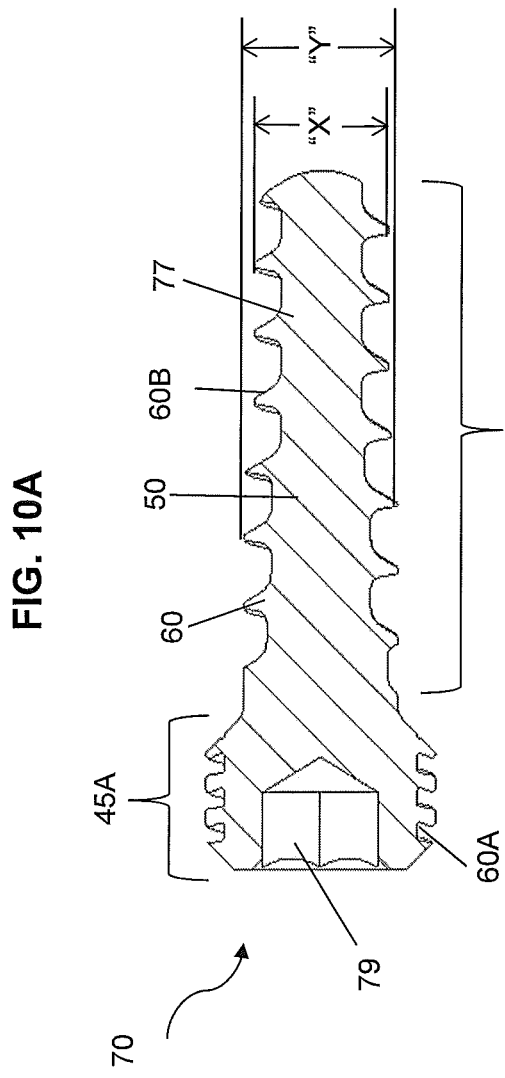
FIG. 10B illustrates a cross-section view of an embodiment of an interacting element having a first body component and a second body component.

FIG. 10A and FIG. 10B illustrates an embodiment of fastener element 70 including a body component 50 and a thread component 60. In particular, the fastener element 70 includes a first body component 45A and a second body component 45B. The first body component 45A includes a first thread component 60A configured to interface with a plate 80 (not shown). The second body component 45B includes a second thread component 60B configured to interface with bone (not shown). As shown in this embodiment, the body component 50 includes different cross-section diameters as shown by "X" and "Y". Although two cross-section diameters are shown, any number of different cross-section diameters of the body component is contemplated. A body component 50 with varying cross-section diameter provides for optimum anchoring of the assembly to the bone. Also shown in this embodiment is a cutting flute element 77 to facilitate a self-tapping capability. As shown within the first body component 45A, a hex component 79 allows for manipulation and placement of the fastener element such as by using a hex socket. As shown more particularly in FIG. 10B, the thread component 60A includes a one-sided dovetail thread arrangement with variable pitch.

FIG. 11A illustrates an exploded view of a plate 80 including a thread receiving element 84. Each thread receiving element 84 includes an outer receiving surface 85, upper receiving surface 86, inner receiving surface 87, and lower receiving surface 89. In this particular embodiment, the upper receiving surface 86A is of a different pitch than upper receiving surface 86B to accommodate the varying pitch of the fastener element 70. Thus, the first threads of the fastener element 70 to engage the upper receiving surface 86A of receiving element 84 of the plate 80 have a sliding fit. In contrast, the last threads of the fastener element 70 to engage the upper receiving surface 86B of receiving element 84 of the plate 80 have an interference fit to lock the plate 80 and fastener element 70 together as shown more specifically in FIG. 11B. FIG. 11B illustrates a cross-section view of an embodiment of a fastener element 70 engaged with the thread receiving element 84 of a plate 80. The fastener element 70 shown in FIG. 11B has two-sided dovetail threads 60, i.e., the upper thread surface 62 and a lower thread surface 66 are each of a dovetail shape.

FIG. 12A, FIG. 12B, FIG. 12C illustrate a plate element 80 according to one embodiment of the invention. As shown, plate 80 including one or more aperture elements 71 through which fastener elements 70 engage. A window element 73 provides for intra-operative as well as post-operative visualization. Intra-operative visualization may include, for example, visualization of a bone graft, surgical tools, or other surgical implements during the surgical procedure such as an endplate attached to the plate 80 via fastener elements 70. Post-operative visualization may include, for example, visualization on x-rays subsequent to the surgical procedure.

FIG. 12B illustrates a lordotic curve 75 and FIG. 12C illustrates an endplate curve 76, both of which coincide or match the curvature of certain features such as an endplate or spine.

Figure 13:
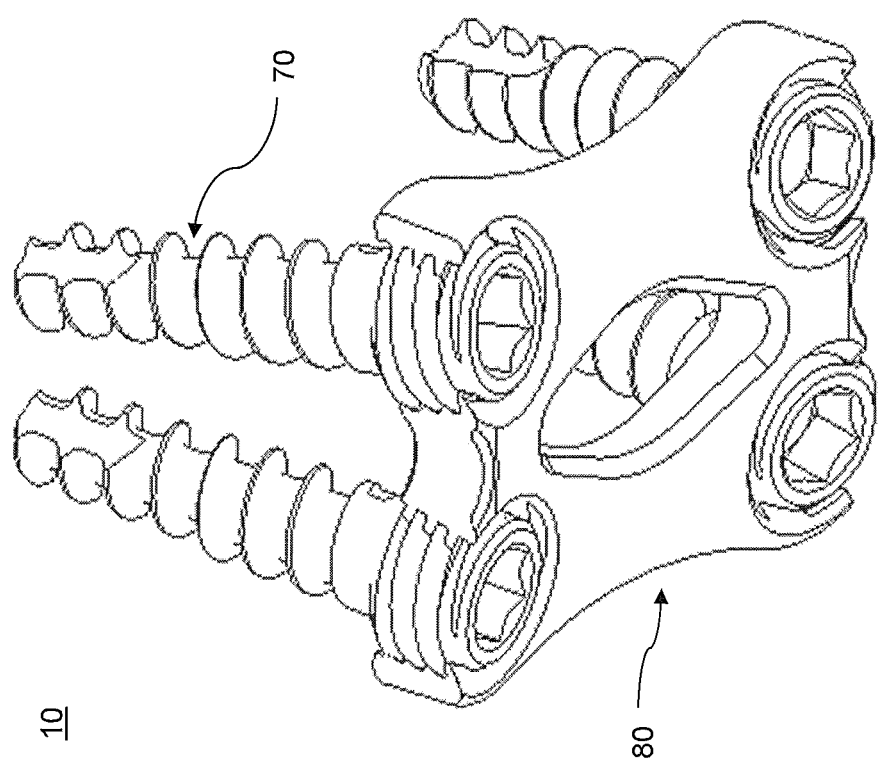
FIG. 13 illustrates an assembly view of a plate element and a plurality of fastener elements.
Figure 14B:
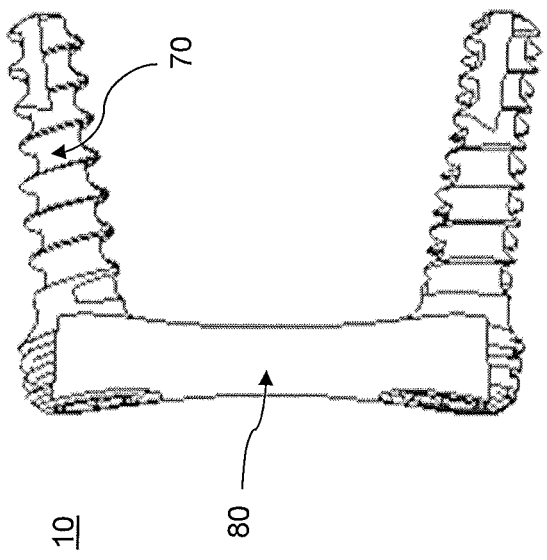
FIG. 14B illustrates a side view of the assembly shown in FIG. 13.
Figure 14C:
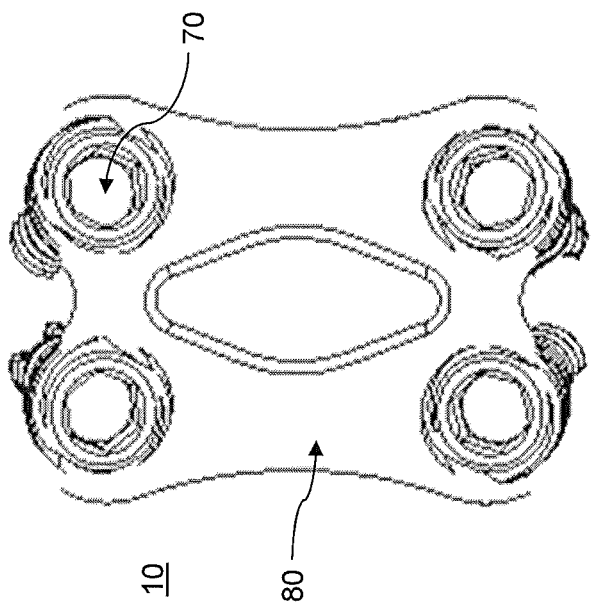
FIG. 14C illustrates a top view of the assembly shown in FIG. 13.
Figure 14A:
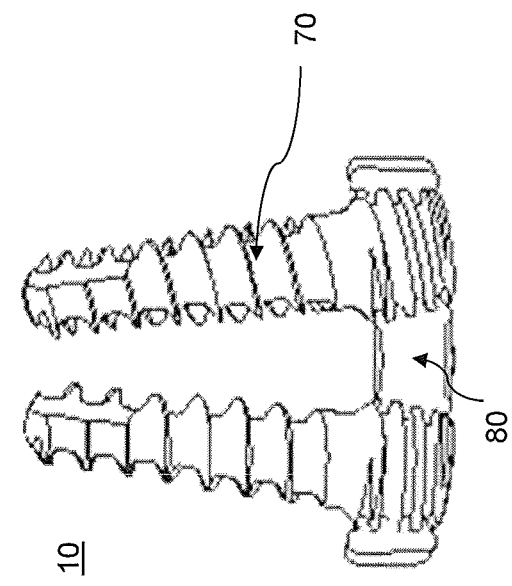
FIG. 14A illustrates a cross-section side view of the assembly shown in FIG. 13.

FIG. 13 illustrates an assembled system 10 including plate element 80 and a plurality of fastener elements 70. FIG. 14A illustrates a cross-section side view of the assembly 10, FIG. 14B illustrates a side view of the assembly 10, and FIG. 14C illustrates a top view of the assembly 10. The trajectories of the fastener elements 70 can be seen in FIG. 13, FIG. 14A, FIG. 14B. The fastener elements 70 are driven with a hex socket until they are flush with the plate 80. In particular, this embodiment of the invention illustrates the aperture elements 71 surround approximately 70% of the end cap element 52 of the fastener element 70 leaving the superior-most and inferior-most parts of the fastener elements 70 exposed. This low profile embodiment allows for secure engagement between the fastener elements 70 and plate 80, which may reduce the risk of pain and discomfort.

While the disclosure is susceptible to various modifications and alternative forms, specific exemplary embodiments of the present invention have been shown by way of example in the drawings and have been described in detail. It should be understood, however, that there is no intent to limit the disclosure to the particular embodiments disclosed, but on the contrary, the intention is to cover all modifications, equivalents, and alternatives falling within the scope of the disclosure as defined by the appended claims.

The invention claimed is:

1. A system for maximizing connection strength between two interacting elements, comprising:
    a first interacting element including a body component and a thread component, wherein the thread component has an upper thread surface, a lower thread surface, an outer thread surface, and the thread component is positioned at least partially around a core body element in a helical shape;
    a second interacting element including a thread receiving element configured to receive the thread component; and
    the thread component having a cross-sectional thread profile, wherein an outer lateral portion of the thread profile has a greater distance between the upper and lower thread surfaces in comparison to the distance between the upper and lower thread surfaces of an inner lateral portion of the thread, thereby maximizing the connection strength between the two interacting elements.

2. The system of claim 1, wherein the thread receiving element is positioned in an outer peripheral surface of the second interacting element.

3. The system of claim 2, wherein the thread receiving element is configured to receive a portion of the thread component that forms less than a full helical turn.

4. The system of claim 3, wherein the thread receiving element is configured to receive only half of a helical turn of the thread component.

5. The system of claim 3, wherein the thread receiving element is configured to receive a portion of the thread component that forms only a third of a helical turn.

6. The system of claim 3, wherein the thread receiving element is configured to receive a portion of the thread component that forms only a fourth of a helical turn.

7. The system of claim 1, wherein the upper thread surface, lower thread surface, and outer thread surface form the profile of the thread component.

8. The system of claim 7, wherein the thread profile of the thread component is larger near the termination end surface relative to the thread profile of the thread component near the origination end surface.

9. The system of claim 1, wherein the thread receiving element includes an upper receiving surface, an inner receiving surface, and a lower receiving surface, which together form a thread receiving profile, and the thread receiving profile is smaller near the receiving termination end relative to the receiving origination end of the thread receiving element.

10. A system for maximizing connection strength between two interacting elements, comprising:
    a first interacting element including a body component and a thread component, wherein the thread component at least partially encircles the body component,
    the thread component having a thread origination end and a thread termination end;
    a second interacting element including a helical-shaped thread receiving element configured to receive the thread component, the thread receiving element having a receiving origination end configured to permit entry of the thread component and a receiving termination end;
    the thread origination end having a cross-sectional area greater than a cross-sectional opening of the receiving origination end or the receiving termination end having a cross-sectional opening less than a cross-sectional area of the thread termination end to impede continued rotation of the thread component with respect to the second interacting element.

11. The system of claim 10, wherein the thread receiving element is positioned in an outer peripheral surface of the second interacting element.

12. The system of claim 11, wherein the thread receiving element is configured to receive a portion of the thread component that forms less than a full helical turn.

13. The system of claim 12, wherein the thread receiving element is configured to receive a portion of the thread component that forms only half of a helical turn.

14. The system of claim 13, wherein the thread receiving element is configured to receive a portion of the thread component that forms only a third of a helical turn.

15. The system of claim 13, wherein the thread receiving element is configured to receive a portion of the thread component that forms only a fourth of a helical turn.

16. The system of claim 10, wherein the thread component includes an upper thread surface, an inner thread surface, and a lower thread receiving surface, which together form the thread profile.

17. The system of claim 10, wherein the thread receiving element includes an upper receiving surface, an inner receiving surface, and a lower receiving surface, which together form a thread receiving profile.

18. A system for maximizing connection strength between two interacting elements, comprising:
- a first interacting element, the first interacting element including a core body element and a thread component is positioned around the core body element in a generally helical shape;
- the thread component having a cross-sectional thread profile comprised of an upper thread surface, a lower thread surface, an outer thread surface;
- a second interacting element, the second interacting element having a main body defined by an upper surface, a lower surface, and an outer peripheral surface that adjoins the upper and lower surfaces and establishes an outer lateral boundary of the second interacting element;
- an aperture disposed through the upper and lower surfaces of the main body, the aperture also passing through the outer peripheral surface of the main body resulting in the aperture having a semicircular shape; and
- a thread receiving element disposed within the aperture, wherein the thread receiving element is configured to receive the thread component, such that a region of the first interacting element, that is diametrically opposed from a region of the thread component received within the thread receiving element when the first interacting element engages the second interacting element, remains exposed to an ambient environment.

19. The system of claim 18, wherein the thread profile of the thread component is larger near the termination end surface relative to the thread profile of the thread component near the origination end surface.

20. The system of claim 18, wherein the thread receiving profile is smaller near the receiving termination end relative to the receiving origination end of the thread receiving element.

* * * * *